United States Patent
Bradley et al.

(10) Patent No.: US 8,059,947 B2
(45) Date of Patent: Nov. 15, 2011

(54) ENVIRONMENTALLY PROTECTED THERMISTOR FOR RESPIRATORY SYSTEM

(75) Inventors: Keith J. Bradley, Atlanta, GA (US); Ryan E. Johnson, Dawsonville, GA (US)

(73) Assignee: Smiths Medical ASD, Inc., Rockland, MA (US)

( * ) Notice: Subject to any disclaimer, the term of this patent is extended or adjusted under 35 U.S.C. 154(b) by 957 days.

(21) Appl. No.: 11/927,077

(22) Filed: Oct. 29, 2007

(65) Prior Publication Data

US 2009/0110378 A1    Apr. 30, 2009

(51) Int. Cl.
*A47J 27/00*    (2006.01)
*G01K 1/16*    (2006.01)

(52) U.S. Cl. .................... 392/441; 374/208

(58) Field of Classification Search .................. None
See application file for complete search history.

(56) References Cited

U.S. PATENT DOCUMENTS

| | | | |
|---|---|---|---|
| 3,402,378 A | | 9/1968 | Shew et al. |
| 3,593,704 A | * | 7/1971 | Schwab ............... 600/500 |
| 3,678,751 A | * | 7/1972 | Mead et al. ............ 338/28 |
| 3,713,899 A | | 1/1973 | Sebestyen |
| 3,738,173 A | * | 6/1973 | Sato ..................... 374/158 |
| 4,098,662 A | | 7/1978 | Schell et al. |
| 4,138,878 A | | 2/1979 | Holmes et al. |
| 4,164,220 A | | 8/1979 | Brickell et al. |
| 4,183,248 A | * | 1/1980 | West ..................... 374/164 |
| 4,464,981 A | | 8/1984 | Stover |
| 4,603,026 A | | 7/1986 | Martin |
| 4,729,672 A | | 3/1988 | Takagi |
| 4,934,831 A | | 6/1990 | Volbrecht |
| 5,165,798 A | | 11/1992 | Watanabe |
| 5,178,468 A | | 1/1993 | Shiokawa et al. |
| 5,348,397 A | * | 9/1994 | Ferrari ................... 374/185 |
| 5,349,946 A | | 9/1994 | McComb |
| 5,392,770 A | | 2/1995 | Clawson et al. |
| 5,667,306 A | * | 9/1997 | Montreuil et al. .......... 374/208 |
| 5,743,646 A | | 4/1998 | O'Connell et al. |
| 5,943,473 A | | 8/1999 | Levine |
| 6,078,730 A | | 6/2000 | Huddart et al. |
| 6,102,565 A | | 8/2000 | Kita et al. |
| 6,272,933 B1 | | 8/2001 | Gradon |
| 6,349,722 B1 | | 2/2002 | Gradon |

(Continued)

FOREIGN PATENT DOCUMENTS

JP    55039006 A    3/1980

(Continued)

OTHER PUBLICATIONS

Manual for Fisher & Paykel Model Nos. MR700, MR720, MR730 Respiratory Humidifiers (Mar. 1998) (48 pages).

(Continued)

*Primary Examiner* — Thor Campbell
(74) *Attorney, Agent, or Firm* — Wood, Herron & Evans, LLP

(57) ABSTRACT

A temperature probe, such as for a respiratory system in which breathable gases are supplied to a patient, includes a housing having a cavity sized to snugly receive therein a generally cylindrical container within which is secured a thermistor, with the container adapted to provide a barrier to moisture. The probe provides a quick temperature response but minimizes migration of moisture to the thermistor notwithstanding the high temperature and heat levels encountered in normal operation of the respiratory system.

42 Claims, 3 Drawing Sheets

U.S. PATENT DOCUMENTS

| | | |
|---|---|---|
| 6,584,972 B2 | 7/2003 | McPhee |
| 6,676,290 B1 | 1/2004 | Lu |
| 6,694,974 B1 | 2/2004 | George-Gradon et al. |
| 6,802,314 B2 | 10/2004 | McPhee |
| 6,918,696 B2 | 7/2005 | Hoshisashi et al. |
| 6,988,497 B2 | 1/2006 | Levine |
| 7,043,979 B2 | 5/2006 | Smith et al. |
| 7,051,733 B2 | 5/2006 | Gradon et al. |
| 7,146,979 B2 | 12/2006 | Seakins et al. |
| RE39,724 E | 7/2007 | Gradon et al. |
| 7,263,994 B2 | 9/2007 | Gradon et al. |
| 7,458,718 B2 | 12/2008 | Krishnamurthy et al. |
| 7,494,274 B2 | 2/2009 | Sisk et al. |
| 7,553,078 B2 | 6/2009 | Hanzawa et al. |
| 2002/0129815 A1 | 9/2002 | McPhee |
| 2002/0139367 A1 | 10/2002 | McPhee |
| 2004/0060558 A1 | 4/2004 | Gradon et al. |
| 2004/0079370 A1 | 4/2004 | Gradon et al. |
| 2006/0137445 A1 | 6/2006 | Smith et al. |
| 2008/0025372 A1 | 1/2008 | Culbertson et al. |
| 2008/0054497 A1 | 3/2008 | Bradley et al. |
| 2008/0054500 A1 | 3/2008 | Bradley et al. |

FOREIGN PATENT DOCUMENTS

| | | |
|---|---|---|
| JP | 60219526 A | 11/1985 |
| JP | 03118432 | 5/1991 |
| JP | 10221176 A | 8/1998 |
| JP | 2001242016 A | 9/2001 |

OTHER PUBLICATIONS

Technical Manual Fisher & Paykel Respiratory Humidifier Model Nos. MR700, MR720, MR730, MR 480 (Mar. 2001) (64 pages).

Allegiance Healthcare 510K No. K993833 for Airlife® Heated Ventilator and Anesthesia Breathing Circuits (5 pages) (Dec. 10, 1999).

Operating Manual for Fisher & Paykel Model Nos. MR700, MR720, MR730 Respiratory Humidifiers (Mar. 1994) (46 pages).

Cardinal Health RT110 Data for Circuits, reprinted from the internet Jun. 3, 2006 (2 pages).

Fisher & Paykel Airway Temperature Probes Instructions for Use (3 pages) (2003).

Official Action issued in related U.S. Appl. No. 11/927,020 mailed Apr. 28, 2010 (11 pages).

Official Action issued in related U.S. Appl. No. 11/927,020 mailed Oct. 4, 2010 (12 pages).

Official Action in related U.S. Appl. No. 11/927,020 mailed Mar. 23, 2011 (14 pages).

Official Action in related U.S. Appl. No. 11/927,020 mailed Jun. 23, 2011 (13 pages).

* cited by examiner

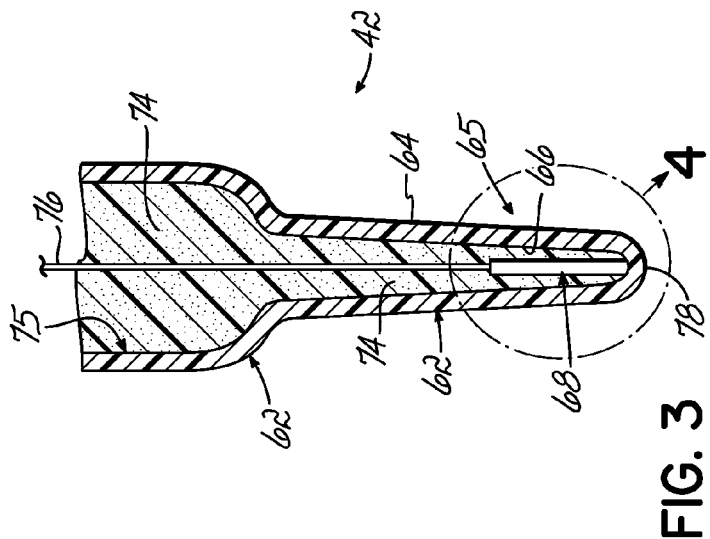
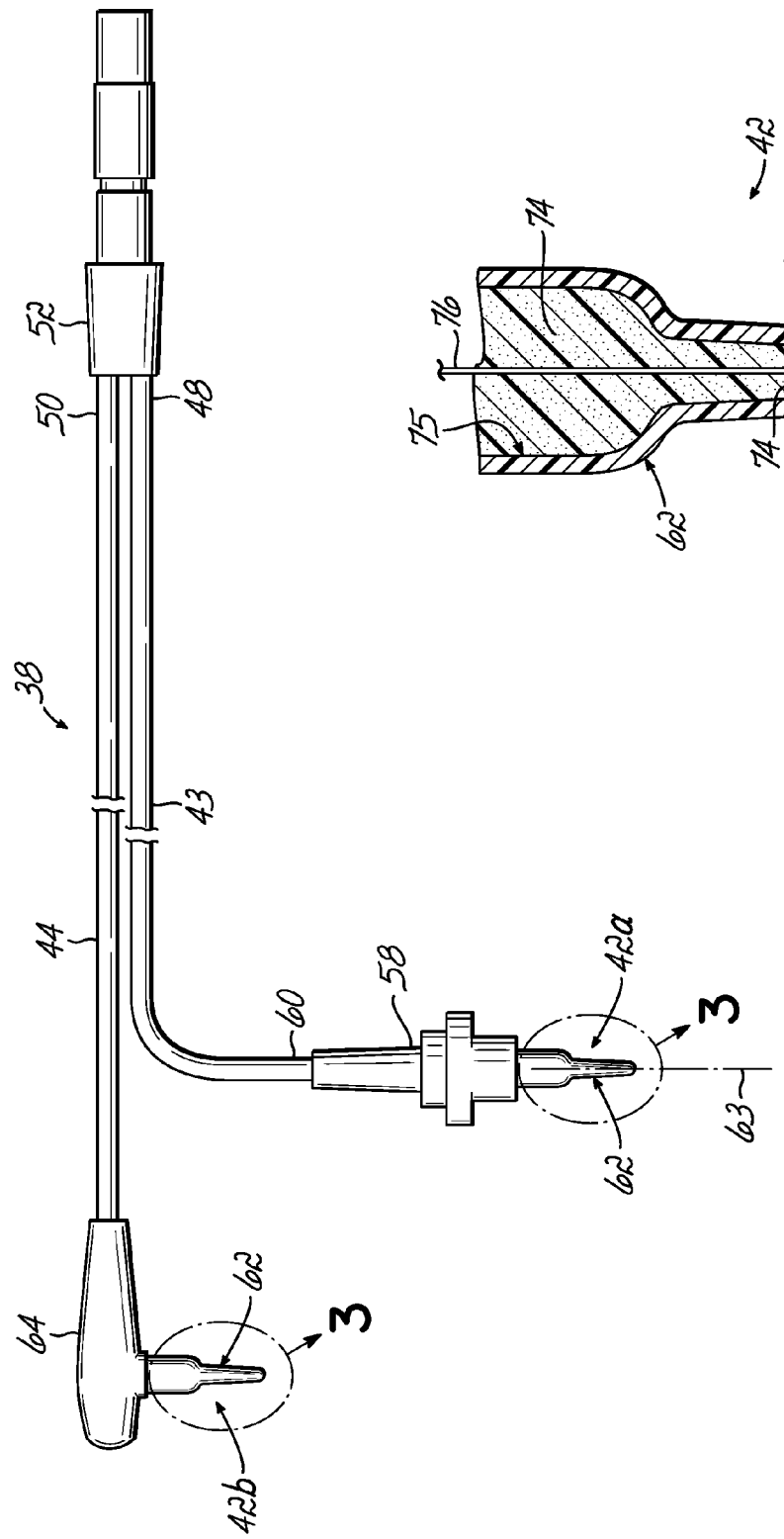
FIG. 2
FIG. 3

ENVIRONMENTALLY PROTECTED THERMISTOR FOR RESPIRATORY SYSTEM

FIELD OF THE INVENTION

The present invention relates generally to respiratory systems incorporating a humidification system, and more particularly, to a temperature probe for sensing the temperature of a breathable gas at desired locations in such a respiratory system.

BACKGROUND OF THE INVENTION

Respiratory systems provide breathable gas, such as oxygen, anesthetic gas, and/or air directly to a patient's mouth, nose, or airway to assist or facilitate breathing by the patient. A ventilator may be used as part of the respiratory system to drive the breathable gas to the patient through an inspiratory limb hose or conduit. An expiratory limb hose or conduit may be provided to allow air to expel from the patient.

It is typically desired to warm and impart humidity to the breathable gas before it is provided to the patient. For that purpose, many respiratory systems include a humidification system having a chamber for holding water and a heater unit to which the chamber may be releasably mounted. The heater unit includes a heater, which may be comprised of one or more heating elements and a metal plate defining a hot plate. A wall of the chamber, such as the bottom surface of the chamber, is thermally conductive and in thermal contact with the hot plate of the heater, to thus heat the water in the chamber. The chamber may be manually refillable, or there may be a water source to selectively fill the chamber as it empties. The breathable gas is coupled to the chamber and is passed through the chamber to be heated and humidified. Examples of heater unit and chamber arrangements are shown in U.S. Pat. Nos. 6,988,497 and 5,943,473. The inspiratory limb carries the heated and humidified gas to the patient and the expiratory limb, if present, carries exhaled air and possibly other gases from the patient. Either or both of the inspiratory and expiratory limbs may be heated such as by heater circuits, which may be comprised of wires running through and along the hose or conduit interior. An example of a breathing circuit with heated limbs is shown in U.S. Pat. No. 6,078,730. In some settings, the limb(s) may not be heated.

Maintaining the desired temperature of gas(es) passing through this type of respiratory system may require adjusting the temperature of the heater in the heater unit and/or the heater circuits in the inspiratory and expiratory limbs in response to thermal feedback from the system. Thus, some respiratory systems include temperature probes at one or more locations, such as for sensing the temperature of the heated and humidified gas supplied to the patient. The temperature probes may be operatively coupled to the heater unit, which then adjusts the power levels to the heater and/or heater circuit(s) based at least in part on the measured temperatures. Current temperature probes for respiratory systems typically include a thermistor, which is packaged in a cylindrical container, such as a polyimide tube, and secured therein with epoxy, all held inside the plastic housing of the temperature probe by a potting compound. Lead wires are electrically coupled to and extend away from the thermistor to be electrically coupled to an associated temperature cable at an opposite end of the housing for electrically communicating with the heater unit.

In respiratory systems, the humidity level of the heated gas is quite high, typically at or near 100%. That high humidity level, coupled with the temperature of the heated gas, is believed to cause significant migration of moisture into the probe housing and against the thermistor. Moisture thus builds up and causes the thermistor to experience electronic drift and/or mechanical compression, such that the temperature readings therefrom become inaccurate and unreliable. In prior thermistor-based probes for respiratory systems, the moisture build-up might happen so rapidly as to render the device generally useless after only a matter of days or weeks. Much longer useful life is necessary. One consideration to reduce the migration of moisture to the thermistor is to encapsulate the thermistor container (or the thermistor if no container is used) in a large bead of glass or epoxy. While the large bead might be expected to reduce moisture problems for the thermistor and thus extend the useful life of the probe, it is believed that such an approach dramatically reduces the temperature response of the thermistor. The temperature readings may thus unduly lag actual changes in temperature, such that the heater unit may not provide adequate temperature regulation of the heater in the heater unit and/or the heater circuit(s) in the breathing circuit limb(s).

SUMMARY OF THE INVENTION

The present invention provides a thermistor-based temperature probe for use in a respiratory system in which the thermistor is environmentally protected to reduce moisture migration thereagainst but without adversely impacting the temperature response thereof. To that end and in accordance with the principles of the present invention, a cavity of the probe housing, such as at the tip end of the probe housing, is sized to snugly receive the thermistor and its associated container so as to situate the container in close thermal relation to the plastic of the probe housing, and the container is adapted to provide a barrier to moisture to minimize migration notwithstanding the high temperature and humidity levels encountered in normal operation of the respiratory system. The container is advantageously cylindrical and may take the form of tube open at both ends or may take the form of a can open at only one end. The thermistor is situated in the tube or can, and epoxy is applied to secure the thermistor therein and close the otherwise open end(s) with the lead(s) extending out from an end.

In the case of a tube, the thermistor is axially centered, i.e., the thermistor is situated generally equidistant from the otherwise open (but for the epoxy) ends so as to balance any generally axial moisture migration paths. In the case of a can, the thermistor is located close to the closed end so as to be far from the otherwise open end defining the most likely moisture migration path. The container may be metal or plastic, the latter advantageously being polyimide. Where the container is metal, the thermistor may advantageously touch the container so as to be in direct thermal contact with the metal thereby enhancing the temperature response of the thermistor to changes in temperature adjacent the probe housing. Where the container is plastic, in accordance with a further aspect of the present invention, the thermistor is to be spaced from the container, so as not to touch the container. To that end, the thermistor may be coated with the epoxy before being installed into the container, so as to create a barrier between the thermistor and the container. Further advantageously, the thermistor is also radially centered so as to be situated generally equidistant from the cylindrical sidewall thereof so as to also balance any generally radial moisture migration paths to the thermistor. The epoxy coating is advantageously applied so as to present a generally uniform maximum thickness (radially) about the thermistor so as to aid in radially centering the thermistor.

The cavity has a cross-dimension (such as a diameter) that closely approximates the cross-dimension of the thermistor container. To that end, and in accordance with another aspect of the present invention, the cavity diameter is advantageously no more than about 0.010 to 0.020 inches larger than the diameter of the thermistor container, such that with the container in place, an annular gap of no more than about 0.005 to 0.010 inches is created around the canister. The spacing between the probe housing and the thermistor container is thus sufficiently small as to not adversely impact heat transfer to the thermistor. The wall thickness of the probe tip end at the cavity is very thin so as to minimize delays in heat transfer as well. Advantageously, the wall thickness at the tip end is no more than about 0.020 inches. With the thermistor container situated in the housing probe cavity, the heat transmission pathway through the probe to the thermistor is quite short, particularly as compared to those of prior thermistor-based probes used with respiratory systems, such that the response time of the thermistor is kept sufficiently fast, while providing an adequate barrier to moisture transmission to at least gain a meaningful useful life of the thermistor before it drifts out of a useful range.

By virtue of the foregoing, there is provided a thermistor-based temperature probe for use in a respiratory system in which the thermistor is environmentally protected to reduce moisture migration thereagainst but without adversely impacting the temperature response thereof. These and other objects, advantages and features of the invention will become more readily apparent to those of ordinary skill in the art upon review of the following detailed description taken in conjunction with the accompanying drawings.

BRIEF DESCRIPTION OF THE DRAWINGS

The accompanying drawings, which are incorporated in and constitute a part of this specification, illustrate an embodiment of the invention and, together with a general description of the invention given above, and the detailed description given below, serve to explain the invention.

FIG. 2 is an enlarged side elevation view, not to scale, of the patient temperature cable of FIG. 1;

FIG. 3 is an enlarged cross-sectional view, not to scale, of a thermistor-based temperature probe of FIG. 2 taken from encircled area 3 in FIG. 2.

DETAILED DESCRIPTION

Figure 1:
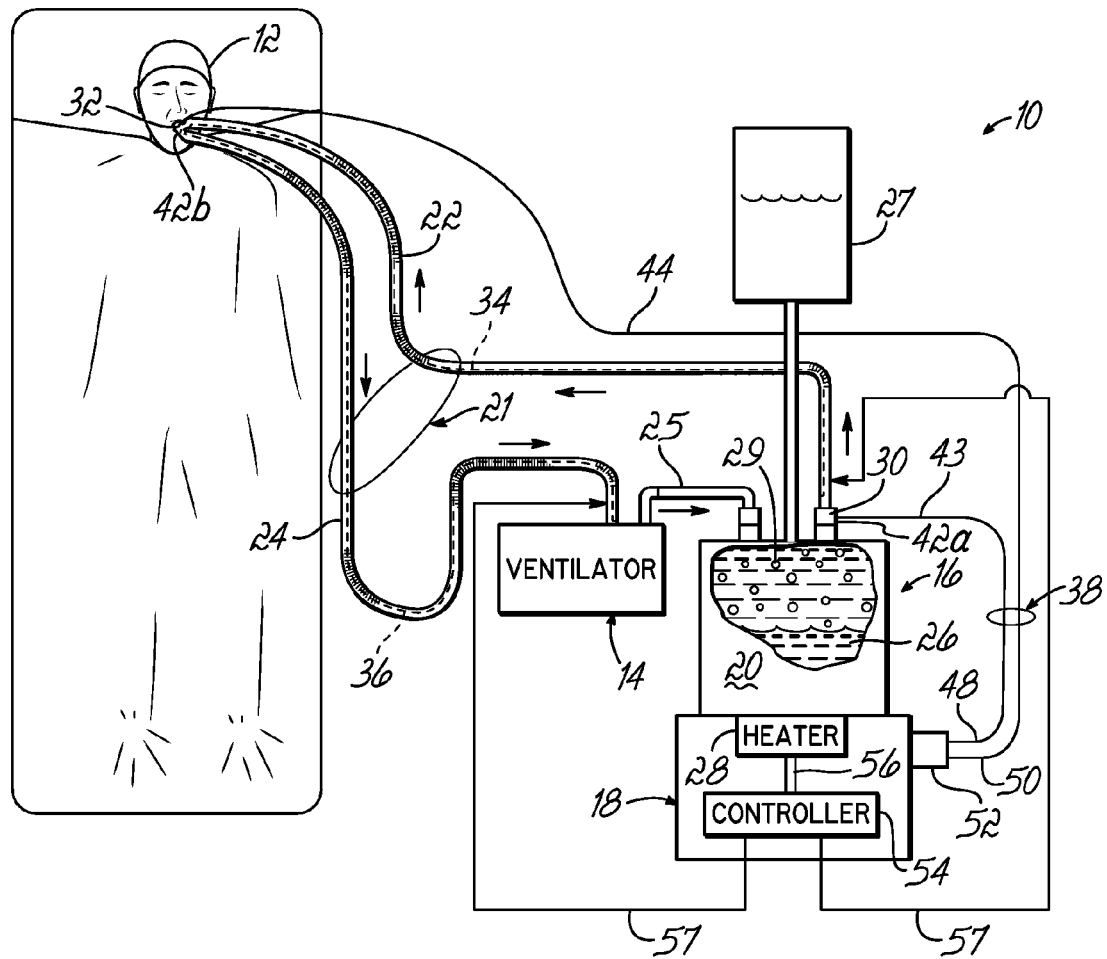
FIG. 1 is a schematic illustration of an exemplary respiratory system including a patient temperature cable including temperature probes constructed in accordance with the principles of the present invention.

FIG. 1 is an exemplary respiratory system 10 for supplying breathable gases to a patient 12. In the illustrated embodiment, the respiratory system 10 includes a ventilator 14, a humidification system 16 having a heater unit 18, a heatable container for water such as a disposable chamber 20, and a breathing circuit 21 having a first elongated hose or conduit 22 defining an inspiratory limb 22 and second elongated hose or conduit 24 defining an expiratory limb. Ventilator 14 drives breathable gas, such as oxygen, anesthetic gas and/or air, through gas conduit 25 and into an inlet of chamber 20. Water 26 is received in chamber 20, either by being poured in manually or automatically from a water supply 27 such as a bag or bottle, which may be vented. Chamber 20 is heated by a heater 28, such as hot plate and one or more heating elements, (not shown), of heater unit 18 to heat up the water 26 therein. Heated water vapor 29 may also be produced within chamber 20 above the level of water 26 therein. The gas from conduit 25 passes over or through the heated water 26 and/or through heated water vapor 29 to become heated and humidified before exiting the chamber 20 as heated and humidified gas. Examples of humidification systems are shown in aforementioned U.S. Pat. Nos. 6,988,497 and 5,943,473, and co-pending U.S. patent application Ser. Nos. 11/469,086 filed Aug. 31, 2006 and Ser. No. 11/469,113 filed Aug. 31, 2006, the disclosures of all four of which are incorporated herein by reference in their entireties.

The heated and humidified gas flows from chamber 20 to the patient 12 through inspiratory limb 22. To this end, a first end of inspiratory limb 22 is coupled to chamber 20 by a connecting member or joint 30, and a second end of inspiratory limb 22 is coupled to a breathing attachment 32 that facilitates delivery of the gas passed therethrough to patient 12. The breathing attachment 32 may couple to an invasive apparatus such as an endotrachael tube, or a non-invasive apparatus such as a mask that promotes gas delivery. If desired, the gas may be further heated while passing through inspiratory limb 22 to breathing attachment 32 by providing a heating circuit 34 associated with inspiratory limb 22. Another heating circuit 36 may be associated with expiratory limb 24, which allows exhaled air and other gas expelled from patient 12 to pass back to ventilator 14, the atmosphere or elsewhere.

Respiratory system 10 also includes a patient temperature cable (PTC) 38 having one or more temperature probes 42 (referenced separately as 42a and 42b where two are used as in the exemplary embodiment shown herein) to provide thermal feedback to heater unit 18. The feedback received from the probes enable heater unit 18 to a vary the power levels to heater 28 and/or heater circuits 34, 36 in order to regulate the temperature of the gas supplied to the patient 12 at a preselected temperature set point conducive to proper respiration and lung viability.

As shown in FIGS. 1 and 2, in one exemplary embodiment patient temperature cable 38 includes a first communication cable 43 having a first temperature probe 42a coupled thereto and a second communication cable 44 having a second temperature probe 42b coupled thereto. First temperature probe 42a may be partially inserted through an opening (not shown) in connecting member 30 and positioned so as to be in thermal communication with the inspiratory gas flowing through inspiratory limb 22, such as in the flow path thereof. Alternatively, probe 42a may be positioned adjacent the flow path of inspiratory limb 22, but in thermal communication with the gas flowing therethrough. First temperature probe 42a is responsive to the temperature of the gas exiting chamber 20 and is electrically coupled to heater unit 18 by first communication cable 43, which has an end 48 electrically coupled to heater unit 18.

Similarly, second temperature probe 42b may be partially inserted through breathing attachment 32 and positioned so as to be in thermal communication with the inspiratory gas flowing through attachment 32 and into patient 12. Second temperature probe 42b may be located directly in the gas flow path of attachment 32 or adjacent the flow path, but in thermal communication with the gas flowing therethrough. Second temperature probe 42b is electrically coupled to heater unit 18 by second communication cable 44, which also has an end 50 electrically coupled to heater unit 18. Ends 48 and 50 may be advantageously secured together by a connector 52 to facilitate coupling the first and second cables 43, 44 to a mating socket (not shown) on heater unit 18.

A controller 54 in heater unit 18 is operatively associated with heater 28 as at 56 (and with heater circuits 34, 36 as at 57) and adapted to control energization of heater 28 (and heater circuits 34, 36 in inspiratory and expiratory limbs 22, 24, respectively) in order to desirably heat water 26 so as to create water vapor 29 by which to heat and humidify the breathable gas passing through chamber 20. A microprocessor or logic circuit (not shown) within controller 54 processes the information from temperature probe(s) 42 to determine whether any adjustments need to be made to the power supplied to heater 26 (or heater circuits 34 and 36). Various details of a controller 54 and associated control logic for adjusting the power supplied to heater 26 and/or heater circuits 34, 36 are provided in the following concurrently-filed U.S. patent applications: U.S. patent application Ser. Nos. 11/926,990; 11/927,000; 11/927,004; 11/927,013; 11/927,054; and 11/927,068. All of the above-mentioned concurrently-filed U.S. patent applications are incorporated herein by reference in their respective entireties.

FIG. 2 illustrates the patient temperature cable 38 in further detail. First temperature probe 42a may be coupled to first communication cable 43 by an overmold 58. More specifically, an end portion 60 of first communication cable 43 is typically inserted into the first temperature probe 42a and secured to an outer housing 62 (FIG. 3) by a conventional fastener, such as a cable tie (not shown). To reinforce the connection, overmold 58 may be molded over end portion 60 and at least a proximal portion of outer housing 62. The end portion 60 and first temperature probe 42a may be coupled substantially along an axis 63 so that patient temperature cable 38 may be properly positioned in the respiratory system 10.

Similarly, second temperature probe 42b may be coupled to second communication cable 44 by an overmold 64. Second temperature probe 42b has the same general design as first temperature probe 42a, as will be described in greater detail below. Due to its particular location in the respiratory system 10, however, second temperature probe 42b may be arranged perpendicularly with respect to second communication cable 44. Thus, the portion of second communication cable 44 inserted into or immediately proximate housing 62, including a right-angle bend and overmold 64, may be configured to accommodate the particular orientation of second temperature probe 42b with respect to second communication cable 44.

Overmolds 58 and 64 provide strain relief so that communication cables 43 and 44 do not separate from their respective temperature probes 42 when the cables are bent or placed in tension. In one embodiment, overmolds 58 and 66 are formed from a thermoplastic resin, such as Santoprene TPV 8281-90MED, and have a durometer of approximately 90 Shore A. The shape and materials of the overmolds 58 and 64 may be selected to serve ergonomic functions as well, making the patient temperature cable 38 easier to grip and temperature probes 42 easier to handle. Furthermore, overmolds 58 and 64 may be designed to act as a moisture barrier to protect wires and other internal components of temperature probes 42 from damage.

Figure 4A:
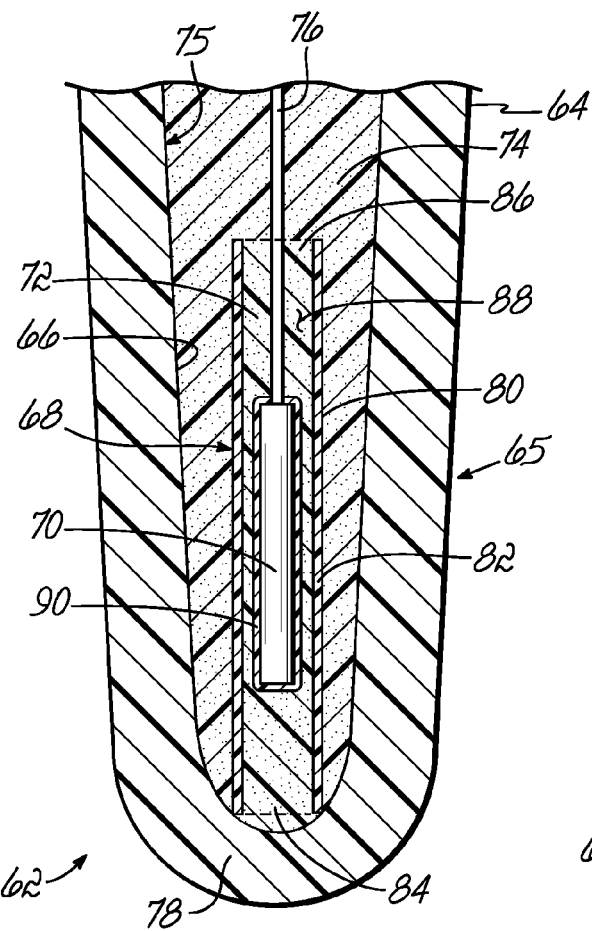
FIGS. 4A and 4B are an enlarged cross-sectional views, not to scale, taken from encircled area 4 of FIG. 3 showing two exemplary embodiments of environmentally protected thermistor-based temperature probes constructed in accordance with the principles of the present invention.
Figure 4B:
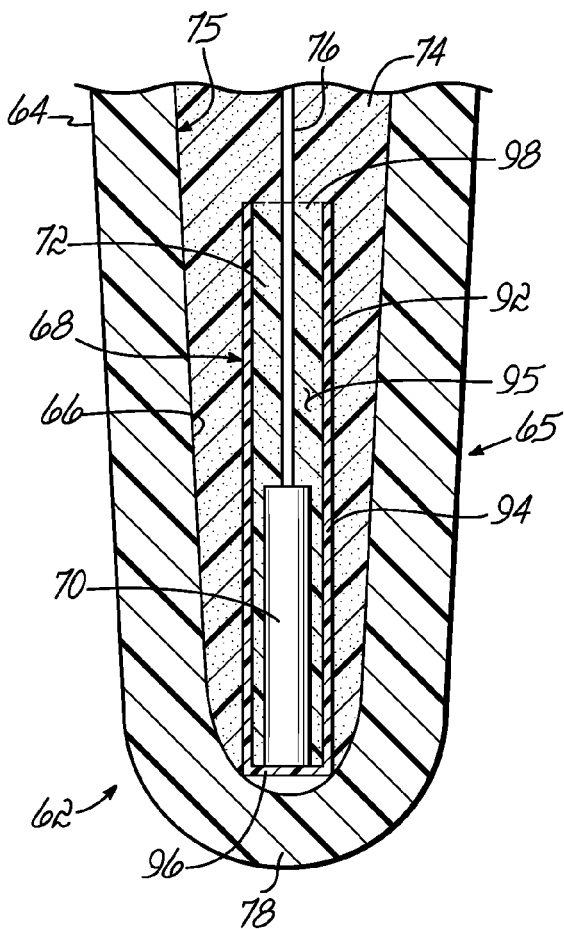

With further reference to FIG. 3, there is shown in cross-section one of temperature probes 42, it being understood that first and second temperature probes 42a and 42b are substantially identical. Temperature probe 42 includes a plastic probe housing 62 having a tip end 65 defining a cavity 66 therein. Situated within cavity 66 is a generally cylindrical container 68 in which a thermistor 70 is secured by epoxy 72 (FIGS. 4A and 4B). Potting compound 74 may fill the interior 75 of probe housing 62 including any aspects of cavity 66 outside of container 68. Electrical leads 76 (only one shown) electrically coupled to thermistor 70 extend out from container 68 and through potting compound 74 to be electrically coupled to the appropriate communication cable 43 or 44 (leads 76 may be positioned to pass closer to the cavity wall or may pass therethrough centrally as shown herein). Cavity 66 is sized to snugly receive container 68 therein so as to situate container 68 in close thermal relation to plastic housing 62 at tip end 64. To that end, the cross dimension of cavity 66 closely approximates the diameter of container 68. In one embodiment, the nominal diameter of cavity 66 is no more than about 0.020, and more advantageously no more than about 0.020 inches, larger than the diameter of container 68. With container 68 radially centered in tip end 64 adjacent the closed bottom 78 thereof, the nominal radial distance between probe housing 62 and container 68 is advantageously no more than about 0.010 inches, and more advantageously no more than about 0.005 inches, such that heat transfer from probe housing 62 to container 68 is not adversely affected.

Probe housing 62 in the area of tip end 64 is also sized to minimize the heat transmission path through probe housing 62 and into cavity 66. To that end, in one embodiment, the wall thickness of probe housing 62, at least in the area of tip end 64, is no more than about 0.020 inches. The small wall thickness of probe housing 62 and the snug fit of container 68 within cavity 66 (with or without potting compound 74 therein), it is believed that the heat transmission pathway through the probe housing 62 to thermistor 70 is sufficiently short that the temperature response of thermistor 70 to changes in temperature outside of probe 42 can be measured in several seconds, as opposed to minutes as is believed to be typical of prior thermistor-based probes used in respiratory systems.

At the same time, and in accordance with the principles of the present invention, thermistor 70 is environmentally protected by adapting container 68 to minimize moisture migration to thermistor 70 notwithstanding the high temperature and humidity levels encountered in normal operation of respiratory system 10. To that end, and with reference to FIG. 4A, container 68 may be in the form of a tube 80 having a generally cylindrical sidewall 82 extending between open ends 84, 86 and defining axially elongated cylindrical space 88 therein. Thermistor 70 is situated in space 88, and held therein by epoxy 72, so as to be secured within container 68 with leads 76 extending out through end 86. Advantageously, thermistor 70 is generally axially centered between ends 84 and 86, such that thermistor 70 is generally equidistant from ends 84 and 86 to thereby balance any generally axial moisture migration paths such as from ends 84, 86. Tube 80 may be metal such that epoxy 72 alone is sufficient to secure thermistor 70 therein and to help seal off ends 84 and 86. Also, thermistor 70 may advantageously touch sidewall 82. Where tube 80 is of plastic, such as polyimide, thermistor 70 is to be encapsulated and also generally radially centered in tube 80 so as to be generally equidistant from sidewall 82 rather than touching same. If desired, and as shown in FIG. 4, before thermistor 70 is placed within space 88, it is coated with a thin encapsulating layer 90 of epoxy, which may be of the same material as epoxy 72. Thin layer 90 helps prevent thermistor 70 from touching sidewall 82 and aids in radially centering thermistor 70 in space 88. To that end, layer 90 may advantageously have a generally uniform maximum thickness (radially) which provides a layer that fits snugly within space 88 in the radial direction. Once thermistor with layer 90 thereon is inserted into space 88 and properly centered (particularly axially), epoxy 72 is applied to secure thermistor 70 in space 88.

Alternatively, and with reference to FIG. 4B, container 68 may take the form of a can 92 having a generally cylindrical sidewall 94 defining axially elongated space 95 closed at one end 96, such as a bottom end, and open at the other end 98, such as a top end. Can 92 could be made by utilizing tube 80 and welding a lid to, or otherwise closing, end 84 thereof to define closed end 96. Alternatively, can 92 can be formed, such as by drawing, so as to have sidewall 94 and closed end 96. With can 92 of metal, thermistor 70 may be placed directly into can 92 in contact with closed end 96 and/or sidewall 92, and then secured therein with epoxy 72 to close off end 98. Advantageously, thermistor 70 is situated close to or at end 96, so as to be as far from otherwise (but for epoxy 72) open end 98 as possible to thereby provide a long moisture migration path from the most likely source of moisture migration, which is considered to be at open end 98. With can 92 of plastic, such as polyimide, thermistor 70 may be pre-coated with layer 90 as above-described before being inserted into can 92 and secured by epoxy 72. Further, thermistor 70 may advantageously be axially and/or radially centered within can 92.

Epoxy 72 may be selected to have relatively high thermal conductivity and/or low durometer so as to provide good heat transfer to thermistor 70 while also avoiding rigid stress forces thereon. One example of an epoxy having those characteristics is Stycast 1090 low density, syntactic foam, epoxy encapsulant available from Emerson & Cuming, a National Starch & Chemical Company. Conversely, potting compound 74 is selected from a material with a relatively low thermal conductivity so as to reduce or minimize heat transfer therethrough thus focusing the heat transfer toward thermistor 70. Potting compound 74 may be a two-part room curable silicone an example of which is Dow MDX4-4210, although other potting compounds may be used depending upon the desired performance characteristics of the probe 42. While it is expected that some potting compound 74 may end up in the radially thin space between container 68 and probe housing 62, a low thermal conductivity potting compound (not shown) could first be applied in the area of tip end 64 to thus provide a dual potting temperature probe as described in concurrently-filed U.S. patent application Ser. No. 11/927,020 the disclosure of which is incorporated herein by reference in its entirety.

Probe housing 62 may be molded from a plastic material that has a relatively high thermal conductivity, such as greater than the thermal conductivity of potting compound 74, but also a relatively low electrical conductivity, excellent chemical resistance and high dimensional accuracy for manufacturing purposes. In one embodiment, outer housing 62 may be molded from a thermoplastic resin reinforced with glass fibers, such as Udel® GF-120 or a similar polysulfone resin available from Solvay Corporation.

In use, temperature probes 42 of patient temperature cable 38 are located in respiratory system 10 as described above and cable 38 is coupled to heater unit 18. Temperature probes 42 are in thermal communication with the heated and humidified gas flowing through inspiratory limb 22 and communicate temperature information of the gas to heater unit 18. Due to the particular construction of temperature probes 42, the probes are capable of quickly responding to thermal changes in the gas, while providing an adequate barrier to moisture transmission to thermistor(s) 70 to at least gain a meaningful useful life of thermistor(s) 70 before it drifts out of useful range. Heater unit 18 may quickly adjust the temperature of heater 26 and/or heater circuits 34, 36 so as to maintain a temperature set point. To benefit from the fast response time of the temperature probes 42, heater 26 may be constructed so as to have a similar response time, i.e., heater 26 is capable of quickly heating up or cooling down. One such heater 26 capable of utilizing the improved response time of the temperature probes 42 is disclosed in concurrently filed U.S. patent application Ser. No. 11/926,982 which is incorporated by reference herein in its entirety. The quick response time of both the temperature probes and heater provide enhanced control over the heating and humidification of the breathable gas(es) to maintain a close tolerance to the pre-selected set point conditions that constitutes a considerable improvement over the set point tolerances achieved in prior respiratory systems.

By virtue of the foregoing, there is provided a thermistor-based temperature probe for use in a respiratory system in which the thermistor is environmentally protected to reduce moisture migration thereagainst but without adversely impacting the temperature response thereof.

While the present invention has been illustrated by a description of an embodiment thereof and specific examples, and while the embodiment has been described in some detail, it is not intended to restrict or in any way limit the scope of the appended claims to such detail. Additional advantages and modifications will readily appear to those skilled in the art. For example, while cable 38 has been shown having two cables 43 and 44 coupled to respective first and second probes 42a and 42b, it will be appreciated that cable 38 might have only one of cables 43 or 44 and its associated probe 42. Additionally, it will be appreciated that while temperature probes 42 have been described in the context of a respiratory system having a humidification system, the temperature probe of the present invention may be utilized in a wide variety of applications for which it is desired to measure temperature in a heated and highly humid environment. The invention in its broader aspects is therefore not limited to the specific details, representative apparatus and methods and illustrative examples shown and described. Accordingly, departures may be made from such details without departing from the scope or spirit of the general inventive concept.

Having described the invention, what is claimed is:

1. A temperature probe comprising:
   a thermistor,
   a generally cylindrical container having first and second ends and an axially elongated space between the first and second ends, and epoxy securing the thermistor between the first and second ends and within the axially elongated space of the container, the container adapted to provide a barrier to minimize moisture migration to the thermistor;
   a plastic housing being sized to envelop the container therein and defining a cavity having a cross-dimension sized to approximate a diameter of the container, the container being snugly received in the cavity; and
   potting compound in the cavity of the plastic housing outside of the container, the potting compound holding the container within the plastic housing.

2. The temperature probe of claim 1, the container being a tube having open first and second ends, the epoxy closing off the first and second ends.

3. The temperature probe of claim 2, the thermistor being generally axially centered in the axially elongated space.

4. The temperature probe of claim 3, the thermistor being generally radially centered in the axially elongated space.

5. The temperature probe of claim 4, the tube being plastic.

6. The temperature probe of claim 5, the thermistor being encapsulated in a thin layer of epoxy in addition to the epoxy securing the thermistor in the axially elongated space.

7. The temperature probe of claim 3, the tube being plastic.

8. The temperature probe of claim 7, the thermistor being encapsulated in a thin layer of epoxy in addition to the epoxy securing the thermistor in the space.

9. The temperature probe of claim 2, the tube being metal.

10. The temperature probe of claim 9, the thermistor in contact with the tube.

11. The temperature probe of claim 1, the container being a can having a closed first end and an open second end, the open second end being closed off by the epoxy.

12. The temperature probe of claim 11, the can being plastic.

13. The temperature probe of claim 11, the can being metal.

14. The temperature probe of claim 13, the thermistor being at the closed first end spaced away from the open second end.

15. The temperature probe of claim 1 in combination with a heater adapted to heat a container of water through which said gas passes and becomes heated and humidified; and a controller operatively coupled to the heater, the temperature probe operatively coupled to the controller.

16. The temperature probe and heater combination of claim 15, the container being a tube having open first and second ends, the epoxy closing off the first and second ends.

17. The temperature probe and heater combination of claim 16, the thermistor being generally axially centered in the axially elongated space.

18. The temperature probe and heater combination of claim 17, the thermistor being generally radially centered in the axially elongated space.

19. The temperature probe and heater combination of claim 18, the tube being plastic.

20. The temperature probe and heater combination of claim 19, the thermistor being encapsulated in a thin layer of epoxy in addition to the epoxy securing the thermistor in the axially elongated space.

21. The temperature probe and heater combination of claim 17, the tube being plastic.

22. The temperature probe and heater combination of claim 21, the thermistor being encapsulated in a thin layer of epoxy in addition to the epoxy securing the thermistor in the space.

23. The temperature probe and heater combination of claim 16, the tube being metal.

24. The temperature probe and heater combination of claim 23, the thermistor in contact with the tube.

25. The temperature probe and heater combination of claim 15, the container being a can having a closed first end and an open second end, the open second end being closed off by the epoxy.

26. The temperature probe and heater combination of claim 25, the can being plastic.

27. The temperature probe and heater combination of claim 25, the can being metal.

28. The temperature probe and heater combination of claim 27, the thermistor being at the closed first end spaced away from the open second end.

29. A temperature cable for communicating information to a remote device, comprising:
   a first cable having a first end adapted to be coupled to the remote device; and
   a temperature probe operatively coupled to a second end of the first cable, the temperature probe comprising:
   a thermistor,
   a generally cylindrical container having first and second ends and an axially elongated space between the first and second ends, and epoxy securing the thermistor between the first and second ends and within the axially elongated space of the container, the container adapted to provide a barrier to minimize moisture migration to the thermistor;
   a plastic housing being sized to envelop the container therein and defining a cavity having a cross-dimension sized to approximate a diameter of the container, the container being snugly received in the cavity; and
   potting compound in the cavity of the plastic housing outside of the container, the potting compound holding the container within the plastic housing.

30. The temperature cable of claim 29, the container being a tube having open first and second ends, the epoxy closing off the first and second ends.

31. The temperature cable of claim 30, the thermistor being generally axially centered in the axially elongated space.

32. The temperature cable of claim 31, the thermistor being generally radially centered in the axially elongated space.

33. The temperature cable of claim 32, the tube being plastic.

34. The temperature cable of claim 33, the thermistor being encapsulated in a thin layer of epoxy in addition to the epoxy securing the thermistor in the axially elongated space.

35. The temperature cable of claim 31, the tube being plastic.

36. The temperature cable of claim 35, the thermistor being encapsulated in a thin layer of epoxy in addition to the epoxy securing the thermistor in the space.

37. The temperature cable of claim 30, the tube being metal.

38. The temperature cable of claim 37, the thermistor in contact with the tube.

39. The temperature cable of claim 29, the container being a can having a closed first end and an open second end, the open second end being closed off by the epoxy.

40. The temperature cable of claim 29, the can being plastic.

41. The temperature cable of claim 39, the can being metal.

42. The temperature cable of claim 41, the thermistor being at the closed first end spaced away from the open second end.

* * * * *